(12) United States Patent
Sakuta

(10) Patent No.: US 7,630,476 B2
(45) Date of Patent: Dec. 8, 2009

(54) X-RAY CT SYSTEM AND METHOD OF MANUFACTURING AN X-RAY CT SYSTEM

(75) Inventor: Shigeru Sakuta, Urayasu (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 136 days.

(21) Appl. No.: 11/526,016

(22) Filed: Sep. 25, 2006

(65) Prior Publication Data

US 2007/0071161 A1    Mar. 29, 2007

(30) Foreign Application Priority Data

Sep. 26, 2005   (JP)   ............................. 2005-277224

(51) Int. Cl.
G21K 1/02   (2006.01)
(52) U.S. Cl. .................... 378/149; 378/147; 378/16
(58) Field of Classification Search ............... 378/7, 378/16, 19, 147–149, 154
See application file for complete search history.

(56) References Cited

U.S. PATENT DOCUMENTS

| | | | |
|---|---|---|---|
| 5,099,134 A | 3/1992 | Hase et al. | |
| 5,357,553 A | 10/1994 | Ferlic et al. | |
| 5,965,893 A * | 10/1999 | Tonami et al. | 250/370.11 |
| 5,991,357 A * | 11/1999 | Marcovici et al. | 378/19 |
| 6,181,767 B1 * | 1/2001 | Harootian | 378/19 |
| 6,363,136 B1 * | 3/2002 | Flisikowski et al. | 378/154 |
| 2002/0064252 A1 * | 5/2002 | Igarashi et al. | 378/19 |
| 2003/0155518 A1 * | 8/2003 | Francke | 250/385.1 |
| 2003/0223548 A1 | 12/2003 | Galish et al. | |
| 2005/0117697 A1 * | 6/2005 | Yasunaga et al. | 378/19 |
| 2005/0135562 A1 | 6/2005 | Freund et al. | |

FOREIGN PATENT DOCUMENTS

| | | |
|---|---|---|
| DE | 197 50 935 A1 | 6/1999 |
| EP | 1 713 090 A2 | 10/2006 |
| JP | 10-5207 | 1/1998 |

OTHER PUBLICATIONS

European Patent Office "European Search Report" dated Jan. 19, 2007, issued in counterpart European Patent Application No. 06019978.3-1526.

* cited by examiner

*Primary Examiner*—Edward J Glick
*Assistant Examiner*—Anastasia Midkiff
(74) *Attorney, Agent, or Firm*—Finnegan, Henderson, Farabow, Garrett & Dunner, L.L.P

(57) ABSTRACT

An X-ray CT system according to the invention includes a holding plate which holds X-ray shield plates, a first support plate which supports one short-directional end portion of the holding plate, the first support plate conforming to a bend of the holding plate, a second support plate which supports another short-directional end portion of the holding plate, the second support plate conforming to the bend of the holding plate, and grooves continuously formed on the respective components when the holding plate, the first support plate, and the second support plate are assembled.

3 Claims, 4 Drawing Sheets

X-RAY CT SYSTEM AND METHOD OF MANUFACTURING AN X-RAY CT SYSTEM

CROSS-REFERENCE TO RELATED APPLICATIONS

This application is based upon and claims the benefit of priority from prior Japanese Patent Application No. 2005-277224, filed Sep. 26, 2005, the entire contents of which are incorporated herein by reference.

BACKGROUND OF THE INVENTION

1. Field of the Invention

The invention relates to an X-ray CT system, such as a multislice X-ray CT system, dual X-ray CT system, or cone beam X-ray CT system, for imaging a sectional plane of an inspection target object, and a method of manufacturing an X-ray CT system.

2. Description of the Related Art

With reference to FIG. 7, an X-ray CT system operates as follows. X-ray beams radiated from an X-ray tube are reduced by a collimator into fan-shaped or cone-shaped X-ray beams. Then, the X-ray tube and arcuate collimator and detector (array) arranged opposite to the X-ray tube are rotated about the inspection target object placed in an imaging region, X-ray information transmitted through the inspection target object is detected by the detector, and a signal of the information is processed by a computer, thereby obtaining an X-ray tomograph. X-ray beams radiated from the X-ray tube are of a type that transmits through the inspection target object and a type that scatters through the inspection target object. The collimator is provided in front of the detector to take only the transmitted X-ray information, to remove scatter beams diagonally entering, and to prevent crosstalk from occurring there between. In the collimator, X-ray shield plates are formed of a material less transmissive of X-rays, in correspondence to respective channels, in front of the detectors one-dimensionally or two-dimensionally arranged.

With reference to FIG. 8, the collimator includes an upper support 10, a lower support 12, side columns 16, and an abutment plate 14. These constituent members are independently, preliminarily grooved on the upper support, the lower support and the abutment plate. These grooves allow the insertion of the X-ray shield plates after assembly of the constituent member. The X-ray shield plates are inserted into the grooves of the collimator assembled after grooves are formed in units of the constituent members (see Jpn. Pat. Appln. KOKAI Publication No. 10-5207).

In this case, a step of aligning the grooves in a several hundreds of portions, which are provided to the respective constituent members, is necessary. According to the above-described collimator and a method of manufacturing an X-ray CT system, the groove alignment has to be done on the order of several tens of micrometers, and the number of the portions is as large as several hundreds. Further, grooving is done independently in units of the constituent members, so that it takes much processing time. In addition, the respective constituent members are manufactured in the manner that grooves are formed on a planar plate, and the plate is bent into the arcuate shape. As a result, however, a rectangular groove shape is deformed into a wedge shape, making it difficult to insert the X-ray shield plate into the groove. Even when processing is done to increase insertability, an inconvenience still occurs in that looseness or rattle occurs in a deep portion of the groove.

BRIEF SUMMARY OF THE INVENTION

An object of the invention is to provide an X-ray CT system and a method of manufacturing an X-ray CT system, that enable high-accuracy grooving to be accomplished in a short time.

An X-ray CT system and a method of manufacturing an X-ray CT system according to the invention are configured as described below. The system and the method, respectively, can be replaced with a detector and a method of manufacturing an X-ray CT system.

An embodiment of the X-ray CT system has: a holding plate which holds X-ray shield plates; a first support plate which supports one short-directional end portion of the holding plate; a second support plate which supports the other short-directional end portion of the holding plate; and grooves continuously formed on the first support plate, the holding plate, and the second support plate.

Another embodiment of the X-ray CT system has: a holding plate which is bent and which holds X-ray shield plates; a first support plate which supports one short-directional end portion of the holding plate in the manner of following the bend of the holding plate; a second support plate which supports the other short-directional end portion of the holding plate in the manner of following the bend of the holding plate; a connecting member which connects between the first support plate and the second support plate; and grooves continuously formed on the first support plate, the holding plate, and the second support plate.

Still another embodiment of the X-ray CT system has: a first holding plate and a second holding plate arranged opposite to each other at a predetermined spacing; grooves respectively provided in mutually opposite positions of the first and second holding plates; and X-ray shield plates respectively inserted and fixed into the grooves formed on the first and second holding plates.

An embodiment of the method of manufacturing an X-ray CT system, has: a step of assembling a holding plate which holds X-ray shield plates, a first support plate which supports one short-directional end portion of the holding plate, a second support plate which supports the other short-directional end portion of the holding plate, and a connecting member which connects between the first support plate and the second support plate; and a step of forming grooves on the first support plate, the holding plate, and the second support plate in a state that the holding plate, the first support plate, the second support plate, and the connecting member are assembled.

Another embodiment of the method of manufacturing an X-ray CT system, has: a step of bending a first support plate which supports one short-directional end portion of a holding plate which holds X-ray shield plates; a step of bending a second support plate which supports the other short-directional end portion of the holding plate; a step of bending the holding plate in the manner of following the bend of the first support plate and the second support plate; a step of assembling the holding plate, the first support plate, the second support plate, and a connecting member that connects between the first support plate and the second support plate; a step of forming grooves on the first support plate, the holding plate, and the second support plate in a state that the holding plate, the first support plate, the second support plate, and the connecting member are assembled; and a step of inserting the X-ray shield plates, respectively, into the grooves.

Still another embodiment of the method of manufacturing an X-ray CT system, has: a step of arranging a first holding plate and a second holding plate to be opposite to each other at a predetermined spacing; a step of forming grooves respectively in mutually opposite positions of the first and second holding plates; and a step of inserting X-ray shield plates, respectively, into the grooves.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
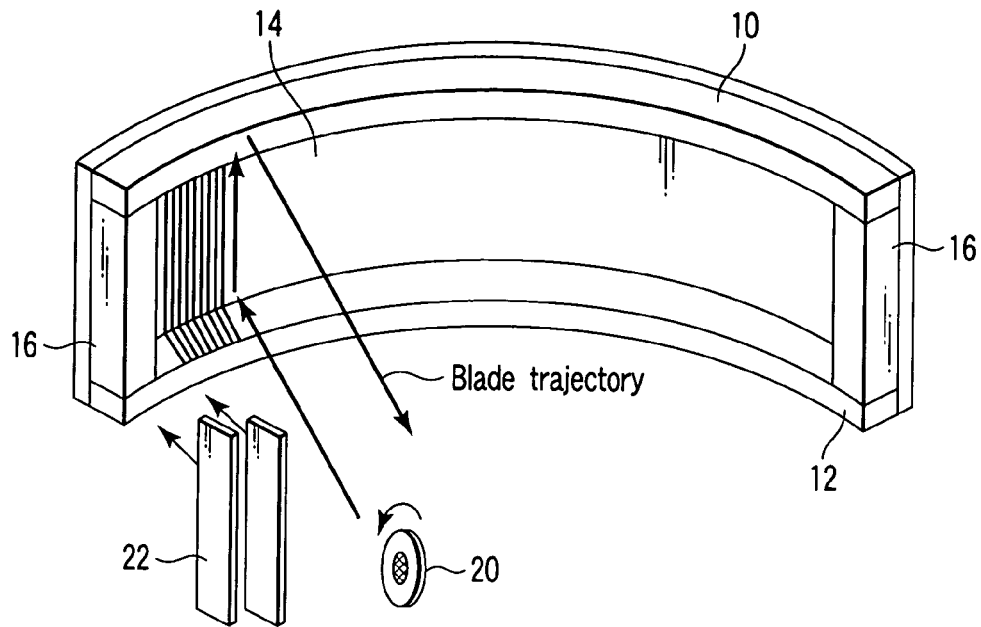
FIG. 1 is a perspective view showing a detector according to an embodiment of the invention.

FIG. 1 is a perspective view of a detector of an X-ray CT system according to an embodiment of the invention, in which upper and lower supports 10 and 12, an abutment plate 14, and side columns 16 are assembled. Positional relations of the constituent members will be described hereinbelow.

The upper support 10 (first support plate) is provided to an upper portion of the abutment plate 14 (holding plate), and the lower support 12 (second support plate) is provided to a lower portion of the abutment plate 14. The upper support 10 and the lower support 12 each have a curvature, and the abutment plate 14 is assembled to follow suit with the upper support 10 and the lower support 12. The side columns 16, respectively, are provided between the upper support 10 and the lower support 12 in two end portions of the abutment plate 14. Thereafter, grooves are formed, and X-ray shield plates 22 are inserted into the grooves.

A first embodiment will be described further hereinbelow with reference to FIG. 1. The abutment plate 14 is provided to arcuate portions on external sides of the respective upper and lower supports 10 and 12. In the state where the abutment plate 14, the upper support 10, the lower support 12, and the side columns 16 are assembled, the abutment plate 14, and the upper and lower supports 10 and 12 are continuously grooved by a blade 20. The grooves are formed by the blade 20 moved from the inner sides of the circular arcs of these constituent members along the vertical direction to forming portions of the abutment plate 14. As shown by the arrow in the drawing, the blade 20 is first moved along the direction of the abutment plate 14 to the lower support 12, thereby to form grooves on the lower support 12. Thereafter, the blade 20 is moved upward, thereby to form grooves on the abutment plate 14. Then, the blade 20 is moved along the direction to be apart from the abutment plate 14 in order to form grooves on the upper support 10. In this manner, grooves of the plurality of constituent members can be continuously formed.

Figure 2:
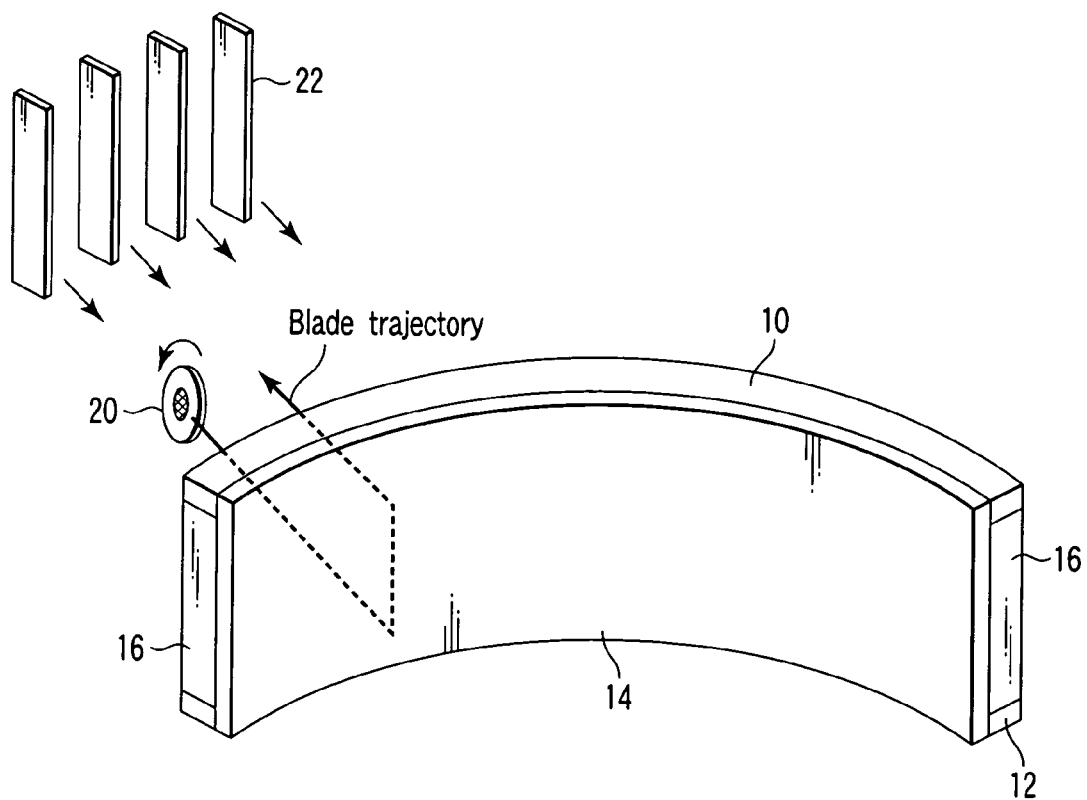
FIG. 2 is a perspective view showing a detector according to an embodiment of the invention.

A second embodiment will be described hereinbelow with reference to FIG. 2. In the second embodiment, the abutment plate 14 is provided to the arcuate portions on the inner sides of the upper and lower supports 10 and 12. The blade 20 is moved from the outer sides of the circular arcs of these constituent members along the vertical direction to forming portions of the abutment plate 14, thereby to form grooves on the lower support 12. This is similar to the case in the first embodiment. Thereafter, the blade 20 is moved upward, thereby to form grooves on the abutment plate 14. Then, the blade 20 is moved along the direction to be apart from the abutment plate 14 in order to form grooves on the upper support 10.

A third embodiment will be described hereinbelow with reference to FIGS. 3A to 3C. The third embodiment relates to the shape of the abutment plate 14. As shown in the drawings, unlike the case in the first and second embodiments in which the grooves are formed on the overall surface of the abutment plate 14, the grooves are formed on part of the abutment plate 14 in the third embodiment. The blades 20 which form the grooves move in the direction of the arrows shown in FIGS. 3A to 3C, respectively.

Figure 3A:
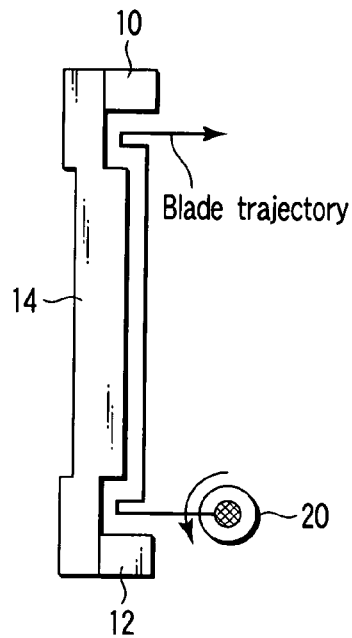
FIGS. 3A to 3C are cross sectional views individually showing shapes of abutment plates according to an embodiment of the invention.

FIG. 3A shows that a protrusion portion is provided in a portion of the abutment plate 14 other than the two end portions thereof, and grooves are formed only in the protrusion portion. The surface opposite to the surface of the protrusion portion forms a recess portion. The surface portions are thus formed so that the amount of X-ray beams attenuated on the abutment plate 14 are made to be the same.

Figure 3B:
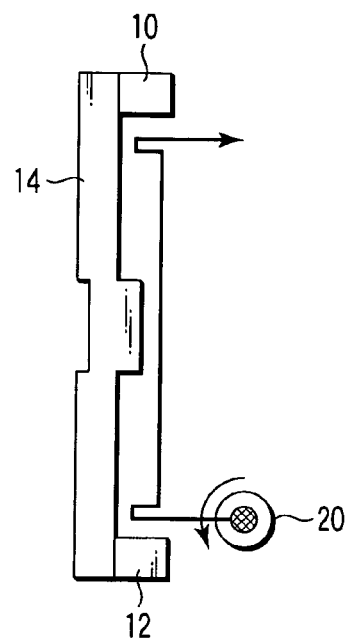

FIG. 3B shows a protrusion portion is provided in a near-center portion of the abutment plate 14, and grooves are formed only in the protrusion portion. The surface opposite to the surface of the protrusion portion forms a recess portion, thereby to equalize maintain the thickness of the abutment plate 14 to be the same. In the FIG. 3B, while the protrusion portion is provided in the near-center portion of the abutment plate 14, it is not limited to the near-center portion, and it can be provided in a position offset therefrom.

Figure 3C:
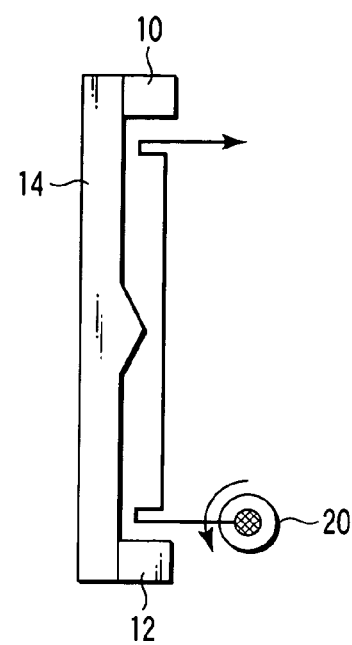

In FIG. 3C, while not having a length as shown in FIG. 3B, a protrusion portion is provided in a near-center portion of the abutment plate 14 to the extent of being a minimum target of position determination, and grooves are formed in the protrusion portion. The protrusion portion is provided to continually vary. This is because, when an irregularity or step, i.e., discontinuous point, is caused on the abutment plate 14, detector linearity (linear relationship between the X-ray intensity and the detector output voltage; that is, inclination) varies at the discontinuous point, thereby making it impossible to obtain an accurate image.

Figure 4:
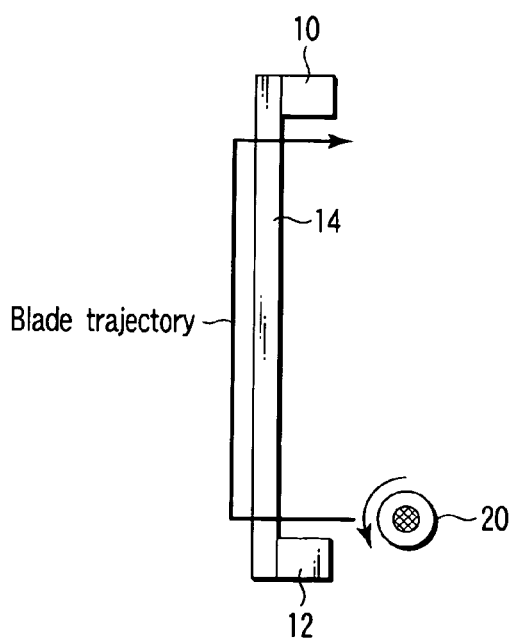
FIG. 4 is a cross sectional view showing a shape of an abutment plate according to an embodiment of the invention.

A fourth embodiment will be described hereinbelow with reference to FIG. 4. In the fourth embodiment, unlike the case of the first and second embodiments in which the grooves are formed to the abutment plate 14, cut-through openings are formed by the blade 20 on the abutment plate 14, thereby to provide slits to the abutment plate 14. With the slits, positional alignment of the X-ray shield plates 22 is carried out. In this case, a thin material is sufficient to form the abutment plate 14.

Figure 5:
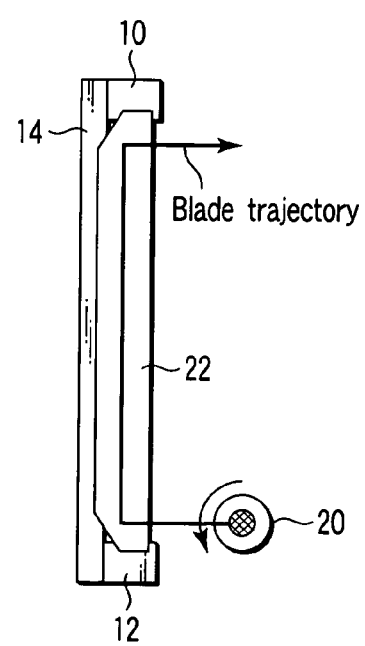
FIG. 5 is a cross sectional view showing a shape of an X-ray shield plate according to an embodiment.

A fifth embodiment will be described hereinbelow with reference to FIG. 5. This embodiment relates to the shape of the X-ray shield plate 22. The shape is a feature in that corners of the X-ray shield plate 22 on the side to be in contact with the abutment plate 14 are angled. As such, advantages are offered in that the X-ray shield plate 22 can easily inserted into the groove, and the processing time can be reduced since the shape of the abutment plate 14 need not be formed to be complex, unlike the case of FIG. 3A.

A sixth embodiment will be described hereinbelow with reference to FIGS. 6A to 6C. This embodiment is processed by using two holding plates, namely, two abutment plates 24. The abutment plates 24 each have an arcuate shape having a curvature. The two abutment plates 24 are temporarily fitted to maintain the state that the two abutment plates 24 are fitted opposite each other.

Figure 6A:
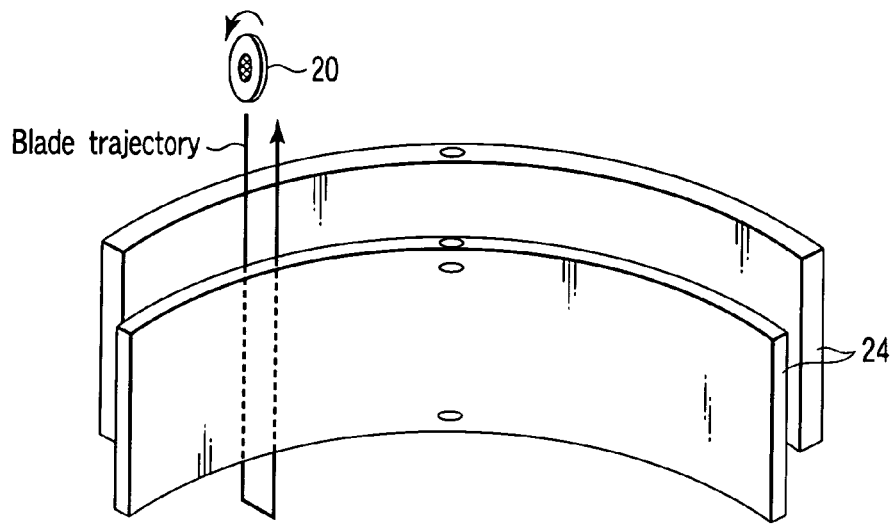
FIGS. 6A to 6C are perspective views each showing a detector according to an embodiment of the invention.
Figure 6B:
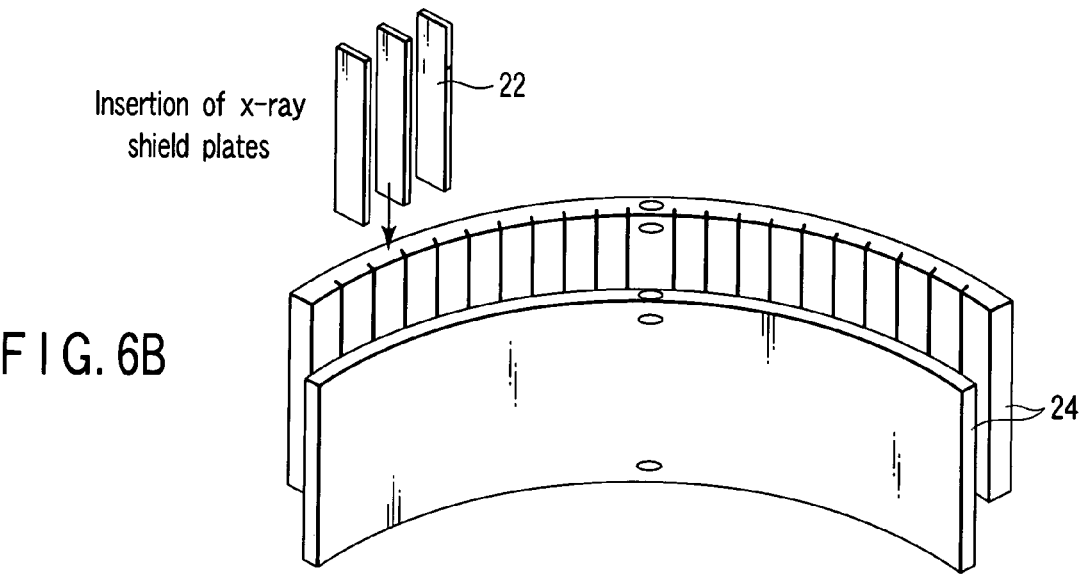
Figure 6C:
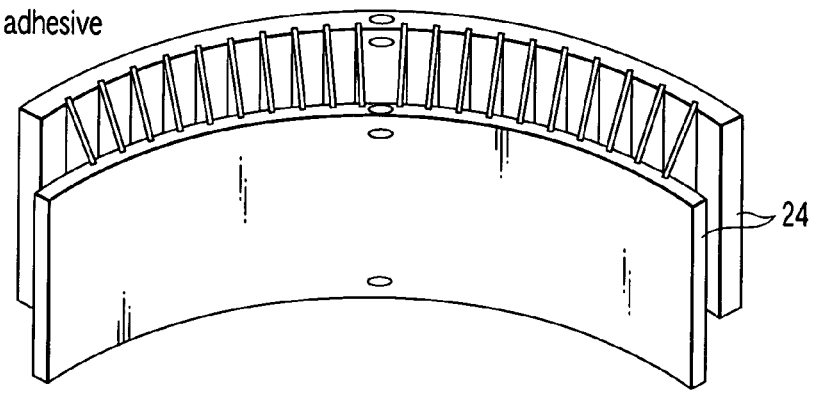
Figure 7:
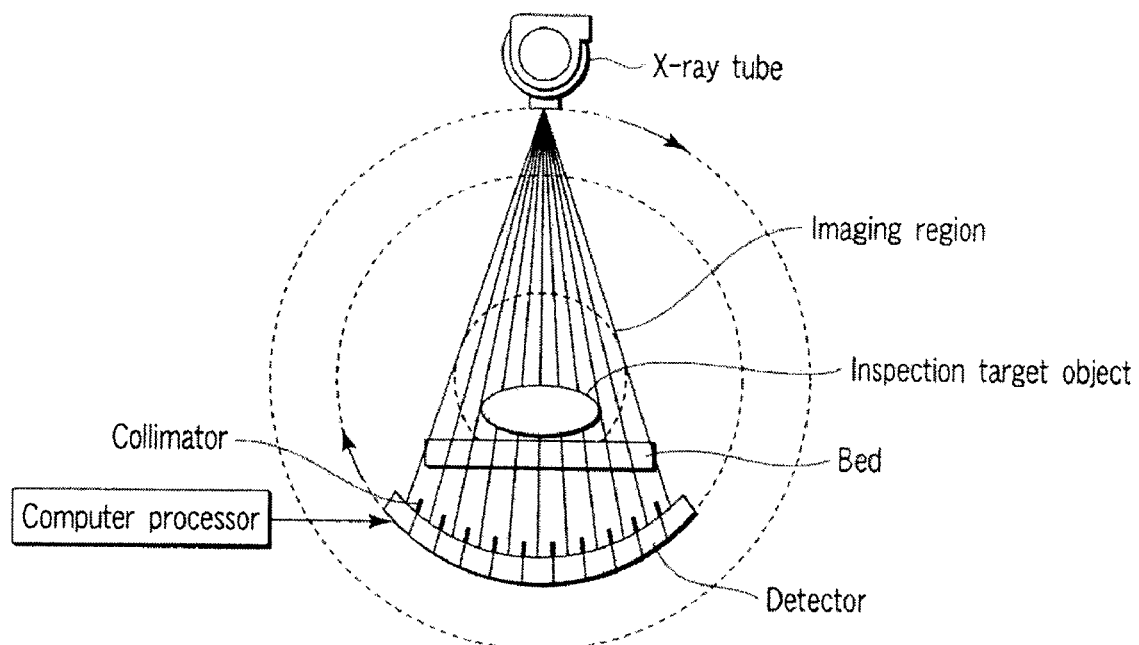
FIG. 7 is an overview of an X-ray CT system according to an embodiment of the invention (which is shown also by way of an embodiment of the prior art)
Figure 8:
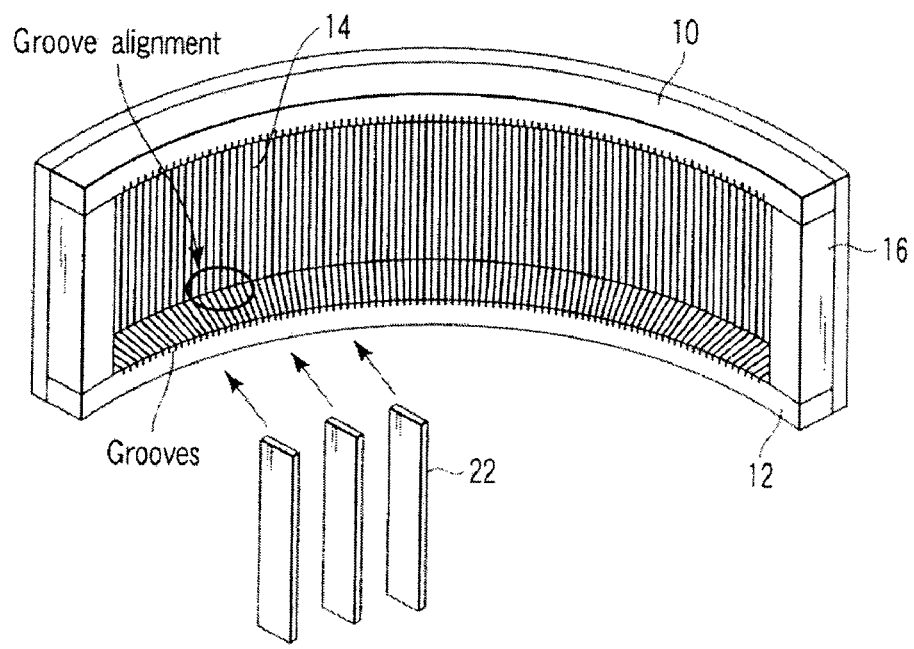
FIG. 8 is a perspective view of a detector according to the prior art.

As shown in FIG. 6A, grooves are formed to the abutment plate 24 in the integral state. Then, as shown in FIGS. 6A to 6C, the respective X-ray shield plate 22 is inserted by maintaining the positions of the two abutment plates 24, whereby the two abutment plates 24 are bonded together with an adhesive. They can be assembled without the upper support, the lower support and the side columns. As a material of the abutment plates 24, glass fiber reinforced plastic (GFRP) is used, but the material may be any one of other substitutable materials.

The present invention is not limited to the embodiments described above, but may be embodied with components modified and altered in various ways in a practicing stage without departing from the spirit or scope of the invention. Further, the plurality of components disclosed in the respective embodiment may be appropriately combined, thereby to enable configuring various other forms of the invention. For example, some components may be omitted from all the components disclosed in the embodiments. Further, the components used in the embodiments different from one another may be appropriately combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing an X-ray CT system, comprising:
    assembling a holding plate configured to hold X-ray shield plates, a first support plate configured to support one short-directional end portion of the holding plate, a second support plate configured to support another short-directional end portion of the holding plate, and a connecting member configured to connect the first support plate and the second support plate, the holding plate being made of a single component; and
    forming continuous grooves on the first support plate, the holding plate, and the second support plate when the holding plate, the first support plate, the second support plate, and the connecting member are assembled.

2. A method of manufacturing an X-ray CT system, comprising:
    bending a first support plate configured to support one short-directional end portion of a holding plate, the holding plate being configured to hold X-ray shield plates and being made of a single component;
    bending a second support plate which supports another short-directional end portion of the holding plate;
    bending the holding plate in a manner conforming to the bend of the first support plate and the second support plate;
    assembling the holding plate, the first support plate, the second support plate, and a connecting member that connect the first support plate and the second support plate;
    forming continuous grooves on the first support plate, the holding plate, and the second support plate when the holding plate, the first support plate, the second support plate, and the connecting member are assembled; and
    inserting the X-ray shield plates, respectively, into the grooves.

3. A method of manufacturing an X-ray CT system, comprising:
    arranging a first holding plate opposite to a second holding plate at a predetermined spacing, the first holding plate and the second holding plate each being made of a single component;
    forming continuous grooves in mutually opposite positions of the first and second holding plates, respectively, when assembled; and
    inserting X-ray shield plates, respectively, into the grooves.

* * * * *